United States Patent
Yamada et al.

(10) Patent No.: US 10,058,273 B2
(45) Date of Patent: Aug. 28, 2018

(54) DETECTION DEVICE AND MEASURING APPARATUS

(71) Applicant: SEIKO EPSON CORPORATION, Tokyo (JP)

(72) Inventors: Kohei Yamada, Shiojiri (JP); Megumi Enari, Suwa (JP); Akiko Yamada, Shiojiri (JP)

(73) Assignee: SEIKO EPSON CORPORATION, Tokyo (JP)

( * ) Notice: Subject to any disclaimer, the term of this patent is extended or adjusted under 35 U.S.C. 154(b) by 0 days.

(21) Appl. No.: 15/632,824

(22) Filed: Jun. 26, 2017

(65) Prior Publication Data

US 2018/0014758 A1      Jan. 18, 2018

(30) Foreign Application Priority Data

Jul. 14, 2016  (JP) .................................. 2016-139673

(51) Int. Cl.
  *A61B 5/1455*    (2006.01)
(52) U.S. Cl.
  CPC ................................. *A61B 5/1455* (2013.01)
(58) Field of Classification Search
  CPC .................................................... A61B 5/1455
  USPC ......................................................... 356/39
  See application file for complete search history.

(56) References Cited

U.S. PATENT DOCUMENTS

| | | | | |
|---|---|---|---|---|
| 5,191,891 A | * | 3/1993 | Righter | A61B 5/0404 600/508 |
| 5,289,824 A | * | 3/1994 | Mills | A61B 5/0404 128/904 |
| 7,020,508 B2 | * | 3/2006 | Stivoric | A61B 5/0205 600/390 |
| 9,348,322 B2 | * | 5/2016 | Fraser | G04G 21/025 |
| 9,839,363 B2 | * | 12/2017 | Albert | A61B 5/0205 |
| 2002/0026106 A1 | | 2/2002 | Khalil et al. | |
| 2011/0144470 A1 | * | 6/2011 | Mazar | A61B 5/04085 600/391 |
| 2013/0096395 A1 | * | 4/2013 | Katra | A61B 5/0537 600/301 |
| 2015/0297134 A1 | * | 10/2015 | Albert | A61B 5/681 600/384 |

(Continued)

FOREIGN PATENT DOCUMENTS

| | | |
|---|---|---|
| JP | H08-182658 A | 7/1996 |
| JP | 2003-523793 A | 8/2003 |

(Continued)

*Primary Examiner* — Roy M Punnoose
(74) *Attorney, Agent, or Firm* — Oliff PLC

(57) ABSTRACT

A detection device that includes a light emitting part that outputs coherent light, a first light receiving part that generates the first detection signal according to a light reception level of the coherent light output from the light emitting part and passing through an artery of the measurement site, and a second light receiving part that generates the second detection signal according to the light reception level of the coherent light output from the light emitting part and passing through the artery, wherein the light emitting part, the first light receiving part, and the second light receiving part are provided on a detection surface facing the measurement site and located on a straight line, and are located at an equal distance from the light emitting part on opposite sides to each other with the light emitting part in between.

6 Claims, 4 Drawing Sheets

(56) References Cited

U.S. PATENT DOCUMENTS

2016/0174854 A1    6/2016  Nishida et al.
2016/0331247 A1*  11/2016  Albert ................ A61B 5/0205
2017/0172416 A1*   6/2017  Hashimoto .......... A61B 5/0062

FOREIGN PATENT DOCUMENTS

| JP | 2006-075354 A | 3/2006 |
| JP | 2006-212095 A | 8/2006 |
| JP | 2016-112277 A | 6/2016 |

* cited by examiner

DETECTION DEVICE AND MEASURING APPARATUS

BACKGROUND

1. Technical Field

The present invention relates to a technology for measuring biological information.

2. Related Art

In related art, various measurement techniques of non-invasively measuring biological information by light radiation to a living organism are proposed. For example, Patent Document 1 (JP-A-2006-75354) discloses a configuration in which light output from a light emitting window and reflected within a living organism is respectively received by a plurality of light receiving windows and biological information on blood is generated from light reception results.

Now, a depth within a living body at which light reaching a light receiving point from a light emitting point passes changes according to a distance between the light emitting point and the light receiving point. In the configuration in which distances between the light emitting window and the respective light receiving windows are different as disclosed in Patent Document 1, the light output from the light emitting window passes through at different depths from one another within the living organism and reach the respective light receiving windows. Therefore, there is a problem that biological information largely varies according to types of tissues, density of blood vessels, etc. in parts within the living organism through which the light reaching the respective light receiving parts have passed.

Further, depending the positions in which the light emitting window and the light receiving windows are placed with respect to the living organism, there is a problem that it is hard to receive the light passing through the blood within the living organism and accuracy of the biological information on the blood is lower.

An advantage of some aspects of the invention is to generate biological information on blood flow of an artery with higher accuracy.

SUMMARY

A detection device according to a first aspect of the invention is a detection device that generates a first detection signal and a second detection signal used for specification of biological information on blood flow of a measurement site, including a light emitting part that outputs coherent light, a first light receiving part that generates the first detection signal according to a light reception level of the coherent light output from the light emitting part and passing through an artery of the measurement site, and a second light receiving part that generates the second detection signal according to the light reception level of the coherent light output from the light emitting part and passing through the artery, wherein the light emitting part, the first light receiving part, and the second light receiving part are provided on a detection surface facing the measurement site and located on a straight line, and the first light receiving part and the second light receiving part are located at an equal distance from the light emitting part on opposite sides to each other with the light emitting part in between. In the above described configuration, the respective first light receiving part and second light receiving part are provided in the positions at an equal distance from the light emitting part, and thereby, the coherent light reaching the respective first light receiving part and second light receiving part from the light emitting part passes through at nearly equal depths inside of the measurement site. Therefore, compared to a configuration including two light receiving parts at different distances from the light emitting part, the detection signals for higher-accuracy specification of the biological information on the blood flow of the artery may be generated.

In a preferred example of the first aspect, the first light receiving part and the second light receiving part are located at a distance from 0.5 mm to 3 mm from the light emitting part. In the above described configuration, the first light receiving part and the second light receiving part are located at the distance from 0.5 mm to 3 mm from the light emitting part. Therefore, compared to a configuration in which the distance between the respective first light receiving part and second light receiving part and the light emitting part is smaller than 0.5 mm or larger than 3 mm, the first detection signal and the second detection signal having higher SN-ratios can be generated.

In a preferred example of the first aspect, the first light receiving part and the second light receiving part are located at a distance from 1 mm to 1.5 mm from the light emitting part. In the above described configuration, the first light receiving part and the second light receiving part are located at the distance from 1 mm to 1.5 mm from the light emitting part. Therefore, compared to a configuration in which the distance between the respective first light receiving part and second light receiving part and the light emitting part is smaller than 1 mm or larger than 1.5 mm, the first detection signal and the second detection signal having significantly higher SN-ratios can be generated.

A detection device according to a second aspect of the invention is a detection device that generates detection signals used for specification of biological information on blood flow of a measurement site including a plurality of detection parts, each of the plurality of detection parts includes a light emitting part that outputs coherent light, a first light receiving part that generates a first detection signal according to a light reception level of the coherent light output from the light emitting part and passing through the measurement site, and a second light receiving part that generates a second detection signal according to the light reception level of the coherent light output from the light emitting part and passing through the measurement site, wherein the light emitting part, the first light receiving part, and the second light receiving part are provided on a detection surface facing the measurement site and located on a straight line, and the first light receiving part and the second light receiving part are located at an equal distance from the light emitting part on opposite sides to each other with the light emitting part in between, and, of the plurality of detection parts, a straight line connecting the first light receiving part and the second light receiving part of one detection part and a straight line connecting the first light receiving part and the second light receiving part of the other detection part are parallel to each other on the detection surface. In the above described configuration, in each of the plurality of detection parts, like the detection device of the first aspect, the coherent light reaching the respective first light receiving part and second light receiving part from the light emitting part passes through at nearly equal depths inside of the measurement site. Therefore, like the detection device of the first aspect, compared to a configuration including two light receiving parts at different distances from the light emitting part, the detection signals for higher-accuracy specification of the biological information on the blood flow of the artery may be generated. Further, in the second aspect, the plurality of detection parts each including the light emitting part, the first light receiving part, and the second light receiving part are provided, and a plurality of detection signals according to states of different positions of the living organism can be generated.

A measuring apparatus according to a preferred aspect of the invention is a measuring apparatus that specifies biological information on blood flow of a measurement site, including a light emitting part that outputs coherent light to the measurement site, a first light receiving part that generates a first detection signal according to a light reception level of the coherent light output from the light emitting part and passing through an artery of the measurement site, a second light receiving part that generates a second detection signal according to the light reception level of the coherent light output from the light emitting part and passing through the artery, and a specification part that specifies the biological information from the first detection signal and the second detection signal, wherein the light emitting part, the first light receiving part, and the second light receiving part are provided on a detection surface facing the measurement site and located on a straight line, and the first light receiving part and the second light receiving part are located at an equal distance from the light emitting part on opposite sides to each other with the light emitting part in between. In the above described configuration, the distances of the respective first light receiving part and second light receiving part from the light emitting part are equal, and thereby, the coherent light reaching the respective first light receiving part and second light receiving part from the light emitting part passes through at nearly equal depths inside of the measurement site. Therefore, compared to a configuration including two light receiving parts at different distances from the light emitting part, the detection signals for higher-accuracy specification of the biological information on the blood flow of the artery may be generated. In addition, the biological information on the blood flow of the artery can be specified with higher accuracy.

A measuring apparatus according to a preferred aspect of the invention is a measuring apparatus that specifies biological information on blood flow of a measurement site, including a belt for attaching the measuring apparatus to the measurement site, a light emitting part that outputs coherent light to the measurement site, a first light receiving part that generates a first detection signal according to a light reception level of the coherent light output from the light emitting part and passing through an artery of the measurement site, a second light receiving part that generates a second detection signal according to the light reception level of the coherent light output from the light emitting part and passing through the artery, and a specification part that specifies the biological information from the first detection signal and the second detection signal, wherein the light emitting part, the first light receiving part, and the second light receiving part are provided on a detection surface facing the measurement site and located on a straight line along a width direction of the belt, and the first light receiving part and the second light receiving part are located at an equal distance from the light emitting part on opposite sides to each other with the light emitting part in between. In the above described configuration, the respective first light receiving part and second light receiving part are provided in the positions at an equal distance from the light emitting part, and thereby, the coherent light reaching the respective first light receiving part and second light receiving part from the light emitting part passes through at nearly equal depths inside of the measurement site. Therefore, compared to a configuration including two light receiving parts at different distances from the light emitting part, the detection signals for higher-accuracy specification of the biological information on the blood flow of the artery may be generated. In addition, the biological information on the blood flow of the artery can be specified with higher accuracy.

BRIEF DESCRIPTION OF THE DRAWINGS

The invention will be described with reference to the accompanying drawings, wherein like numbers reference like elements.

DESCRIPTION OF EXEMPLARY EMBODIMENTS

Figure 1:
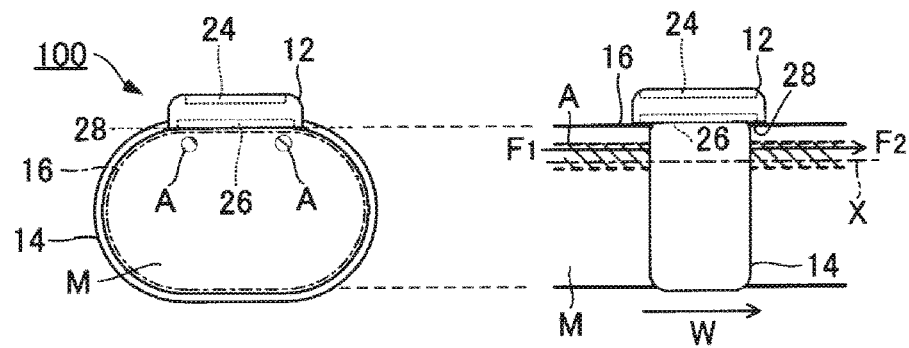
FIG. 1 is a side view of a measuring apparatus according to a preferred embodiment of the invention.

FIG. 1 is a side view of a measuring apparatus 100 according to a preferred embodiment of the invention. The measuring apparatus 100 of the embodiment is a measuring instrument that specifies biological information on blood flow of a subject and attached to a site M to be measured of the body of the subject (hereinafter, referred to as "measurement site"). In the embodiment, blood pressure measured with a wrist of the subject as the measurement site M is exemplified as biological information on blood flow.

The measuring apparatus 100 of the embodiment is a wristwatch-type portable apparatus including a belt 14 wrapped around the measurement site M and a casing part 12 fixed to the belt 14, and can be attached to the wrist of the subject by wrapping the belt 14 around the wrist as an exemplification of the measurement site M. The measuring apparatus 100 of the embodiment is in contact with a surface 16 of the wrist of the subject. An artery A exists inside of the measurement site M. The artery A is e.g. a radial artery along the inside of the radius on the thumb side or an ulnar artery along the ulna of on the little-finger side. The blood in the artery A flows from the upper arm (shoulder) side F1 to the forearm (hand) F2 side as exemplified in FIG. 1.

Figure 2:
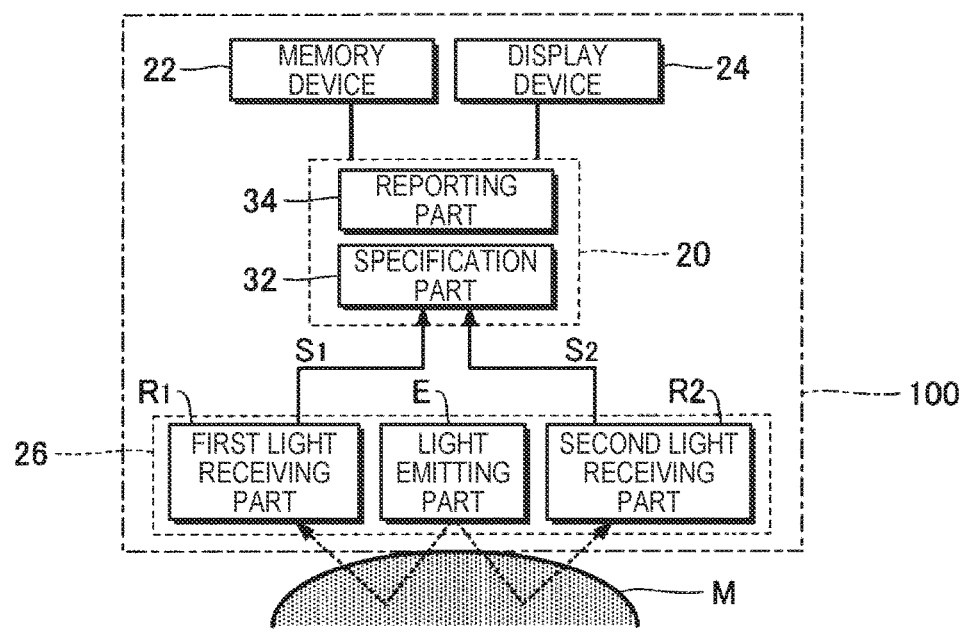
FIG. 2 is a configuration diagram with a focus on functions of the measuring apparatus.

FIG. 2 is a configuration diagram with a focus on functions of the measuring apparatus 100. As exemplified in FIG. 2, the measuring apparatus 100 of the embodiment includes a control device 20, a memory device 22, a display device 24, and a detection device 26. The control device 20 and the memory device 22 are provided inside of the casing part 12. As exemplified in FIG. 1, the display device 24 (e.g. a liquid crystal display panel) is provided on a surface of the casing part 12 (e.g. a surface opposite to the measurement site M) and displays various images including measurement results under the control of the control device 20.

The detection device 26 in FIG. 2 is a sensor module that generates detection signals S according to the states of the measurement site M, and provided on e.g. a surface 28 of the casing part 12 facing the measurement site M (hereinafter, referred to as "detection surface"). The detection surface 28 is a flat surface or curved surface. The detection device 26 of the embodiment generates a first detection signal S1 and a second detection signal S2 used for specification of the biological information on blood flow. The detection device 26 includes a light emitting part E, a first light receiving part R1, and a second light receiving part R2 as exemplified in FIG. 2. The light emitting part E, the first light receiving part R1, and the second light receiving part R2 are provided on the detection surface 28 facing the measurement site M. Note that the first light receiving part R1 and the second light receiving part R2 are collectively described as "light receiving parts R" when it is not necessary to particularly distinguish the first light receiving part R1 and the second light receiving part R2.

The light emitting part E emits light. The light output by the light emitting part E of the embodiment is e.g. coherent light with high coherence. For example, a VCSEL (Vertical Cavity Surface Emitting LASER) that outputs coherent light from the detection surface 28 in a perpendicular direction to the measurement site M is preferably used as the light emitting part E. The light emitting part E of the embodiment outputs coherent light having a wavelength of 850 nm and irradiation intensity equal to or less than 3 mW/cm$^2$ to the measurement site M.

The coherent light output from the light emitting part E enters the measurement site M and is repeatedly reflected and scattered inside of the measurement site M, and exits to the detection surface 28 side and reaches the first light receiving part R1 and the second light receiving part R2. That is, the detection device 26 of the embodiment is a reflective optical sensor such that the light emitting part E, the first light receiving part R1, and the second light receiving part R2 are located on the same side as seen from the measurement site M. The first light receiving part R1 generates the first detection signal S1 according to the light reception level of the coherent light output from the light emitting part E and passing through the artery A of the measurement site M. The second light receiving part R2 generates the second detection signal S2 according to the light reception level of the coherent light output from the light emitting part E and passing through the artery A of the measurement site M. For example, photoelectric conversion elements such as photodiodes (PDs) that receive light on light receiving surfaces facing the measurement site M are preferably used as the first light receiving part R1 and the second light receiving part R2.

The artery A of the measurement site M repeatedly expands and contracts in the cycle equal to that of the heartbeat. The blood flow rate of the blood within the blood vessel differs between expansion and contraction, and the first detection signal S1 and the second detection signal S2 generated according to the light reception levels from the measurement site M are pulse wave signals containing periodic fluctuation components corresponding to a pulsation component (volume pulse wave) of the artery A of the measurement site M. Note that the detection device 26 includes e.g. a drive circuit that drives the light emitting part E by supply of a drive current and an output circuit (e.g. an amplification circuit and an A/D converter) that amplifies and A/D-converts the output signals of the first light receiving part R1 and the second light receiving part R2, however, the respective circuits are not shown in FIG. 1.

Figure 3:
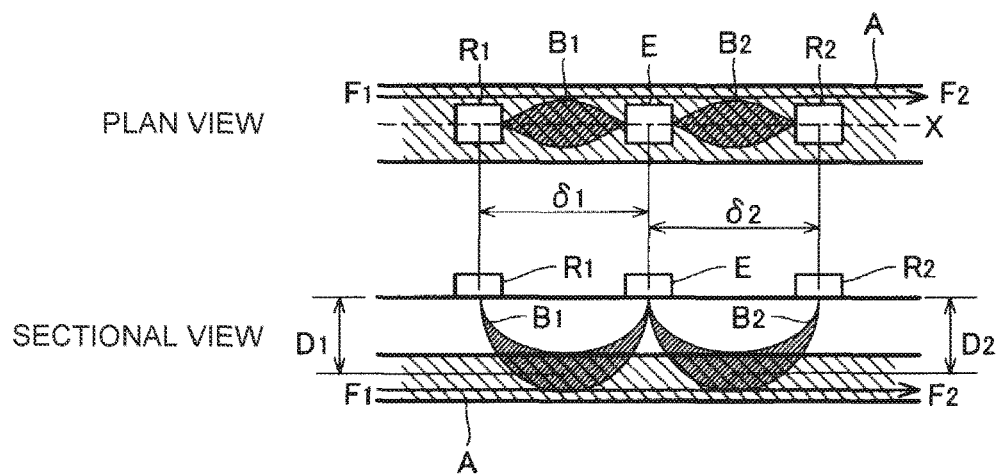
FIG. 3 is an explanatory diagram of positions of a light emitting part, a first light receiving part, and a second light receiving part with respect to an artery.

FIG. 3 is an explanatory diagram of positions of the light emitting part E, the first light receiving part R1, and the second light receiving part R2 with respect to the artery A. As exemplified in FIG. 3, the light emitting part E, the first light receiving part R1, and the second light receiving part R2 are located on a straight line X along the artery A in a plan view (as seen from a direction perpendicular to the detection surface 28). In other words, the configuration may be a configuration in which the light emitting part E, the first light receiving part R1, and the second light receiving part R2 are linearly arranged. The straight line X is a straight line substantially parallel to the direction in which the artery A extends (the axis line direction of the wrist as the measurement site M). Specifically, the respective centers of the light emitting part E, the first light receiving part R1, and the second light receiving part R2 are located on the straight line X in the plan view. In FIG. 3, the case where the light emitting part E, the first light receiving part R1, and the second light receiving part R2 all completely overlap with the artery A in the plan view (are located within a range in the width direction of the artery A) is assumed. As exemplified in FIG. 1, in other words, the straight line X may be a straight line along a width direction W of the belt 14. That is, the light emitting part E, the first light receiving part R1, and the second light receiving part R2 are located on the straight line X along the width direction W of the belt 14. The width direction W of the belt 14 is a lateral direction in the strip-shaped belt 14, and, in other words, may be a direction of the center axis of the cylinder with the belt 14 as a side surface.

In the embodiment, as exemplified in the plan view of FIG. 3, the first light receiving part R1 and the second light receiving part R2 are located on the opposite sides to each other with the light emitting part E in between. In other words, the configuration may be a configuration in which the light emitting part E is located on the straight line X connecting the first light receiving part R1 and the second light receiving part R2. The first light receiving part R1 is located on the upper arm side F1 as seen from the light emitting part E and the second light receiving part R2 is located on the forearm side F2 as seen from the light emitting part E. That is, the first light receiving part R1 is located on the upstream side of the artery A and the second light receiving part R2 is located on the downstream side of the artery A. The above described configuration is employed, and thereby, the first light receiving part R1 and the second light receiving part R2 easily receive the coherent light passing through the artery A.

In FIG. 3, ranges B in which the coherent light reaching from the light emitting part E to the light receiving parts R propagates inside of the measurement site M (hereinafter, referred to as "propagation ranges") are shown. The propagation ranges B (B1, B2) refer to ranges in which light having intensity exceeding a predetermined value is distributed (so-called banana shapes). In FIG. 3, the propagation range B1 of the coherent light reaching from the light emitting part E to the first light receiving part R1 and the propagation range B2 of the coherent light reaching from the light emitting part E to the second light receiving part R2 are shown. As exemplified in FIG. 3, the propagation range B1 and the propagation range B2 tend to overlap with the range in which the artery A extends in the plan view.

As described above, in the embodiment, the light emitting part E, the first light receiving part R1, and the second light receiving part R2 are located on the straight line along the artery A, and thereby, for example, compared to a configuration in which the light emitting part E, the first light receiving part R1, and the second light receiving part R2 are not along the artery A, the coherent light passing through the artery A is easily received in the first light receiving part R1 and the second light receiving part R2. Therefore, the detection signals S for higher-accuracy specification of the biological information on the blood flow of the artery A may be generated.

Now, depths D (distances from the surface 16 of the measurement site M) of the propagation ranges B depend on distances δ between the light emitting part E and the light receiving parts R. The distances δ are e.g. distances between centers of the light emitting part E and the light receiving parts R. There is a tendency that, as the distances δ are larger, the depths D reached by the light inside of the measurement site M increase (the light reaches the deeper positions). When a depth D through which the coherent light received by the first light receiving part R1 passes and a depth D through which the coherent light received by the second light receiving part R2 passes are different, the types of inner tissues (e.g. epidermis, dermis), density of blood vessels, etc. of the measurement site M are different, and optical characteristics including absorbance and density may be different. In consideration of the above described circumstances, in the embodiment, as exemplified in FIG. 3, the distance δ1 between the light emitting part E and the first light receiving part R1 and the distance δ2 between the light emitting part E and the second light receiving part R2 are made equal. According to the above described configuration, the depth D1 of the propagation range B1 of the coherent light received by the first light receiving part R1 and the depth D2 of the propagation range B2 of the coherent light received by the second light receiving part R2 are nearly equal. Therefore, the detection signals S for higher-accuracy specification of the biological information on the blood flow of the artery A may be generated.

Figure 4:
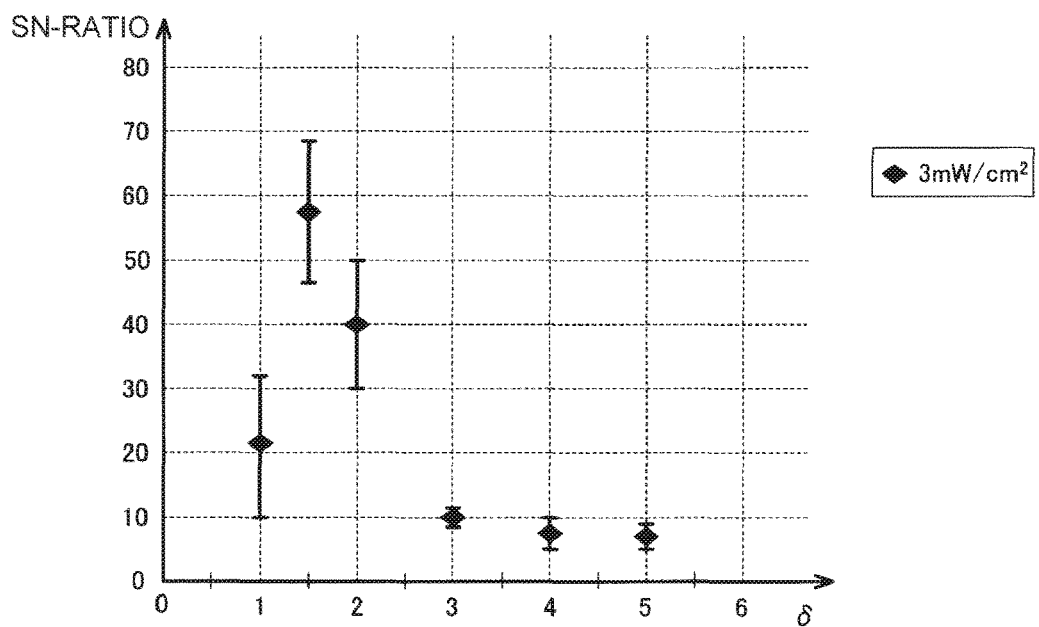
FIG. 4 is a graph of relationships between distances between the light emitting part that outputs coherent light with irradiation intensity of 3 mW/cm$^2$ and the light receiving parts and SN-ratios of detection signals.
Figure 5:
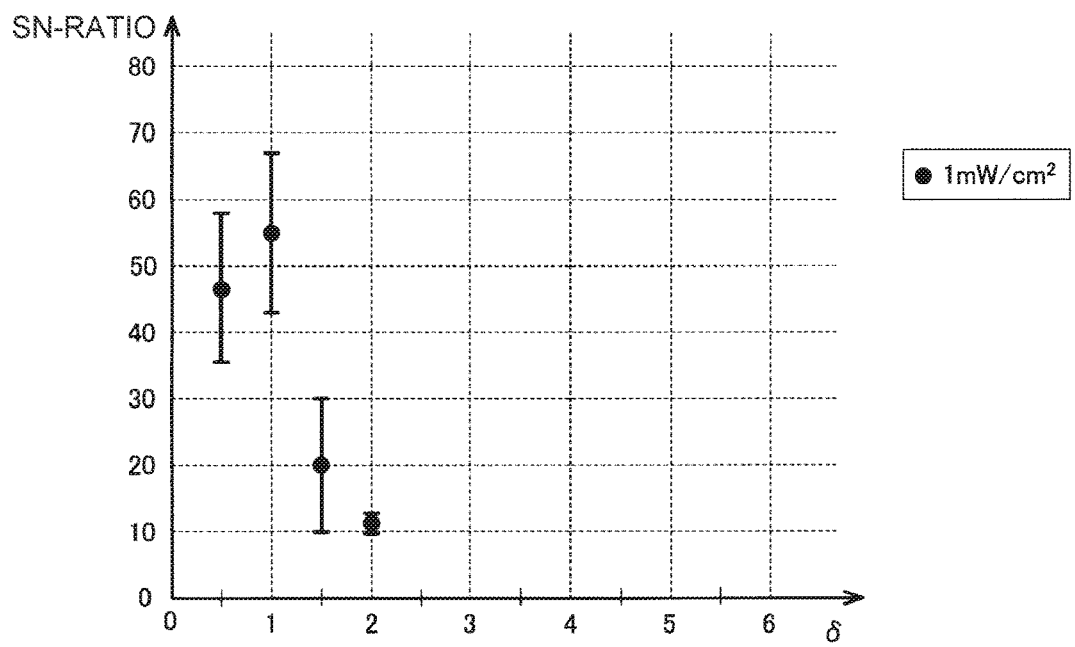
FIG. 5 is a graph of relationships between distances between the light emitting part that outputs coherent light with irradiation intensity of 1 mW/cm$^2$ and the light receiving parts and the SN-ratios of the detection signals.

FIGS. 4 and 5 are graphs of relationships between the distances δ between the light emitting part E and the light receiving parts R and SN-ratios of detection signals S (first detection signal S1 or second detection signal S2) generated by the light receiving parts R. FIG. 4 shows the case where the coherent light is output with irradiation intensity of 3 mW/cm$^2$, and FIG. 5 shows the case where the coherent light is output with irradiation intensity of 1 mW/cm$^2$. The SN-ratio refers to an intensity ratio between a signal component and a noise component. As the SN-ratio is higher, the detection signal S more preferable for the specification of the biological information is generated. As exemplified in FIGS. 4 and 5, the SN-ratios indicate higher values when the distances δ are from 0.5 mm to 3 mm, and more significant when the distances are from 1 mm to 1.5 mm. Therefore, the distance δ1 and the distance δ2 are set from 0.5 mm to 3 mm, and more preferably set from 1 mm to 1.5 mm. The above described configuration is employed, and thereby, the first detection signal S1 and the second detection signal S2 with higher SN-ratios can be generated.

The control device 20 in FIG. 2 is an arithmetic processing unit such as a CPU (Central Processing Unit) or FPGA (Field-Programmable Gate Array) that controls the entire measuring apparatus 100. The memory device 22 includes e.g. a nonvolatile semiconductor memory and stores programs to be executed by the control device 20 and various kinds of data to be used by the control device 20. The control device 20 of the embodiment realizes a plurality of functions (specification part 32, reporting part 34) for measuring blood pressure of the subject by executing the programs stored in the memory device 22. Note that a configuration in which the functions of the control device 20 are distributed in a plurality of integrated circuits or a configuration in which part or all of the functions of the control device 20 are realized by a dedicated electronic circuit may be employed. In FIG. 2, the control device 20 and the memory device 22 are shown as separate elements, however, the control device 20 containing the memory device 22 can be realized by e.g. an ASIC (Application Specific Integrated Circuit) or the like.

Figure 7:
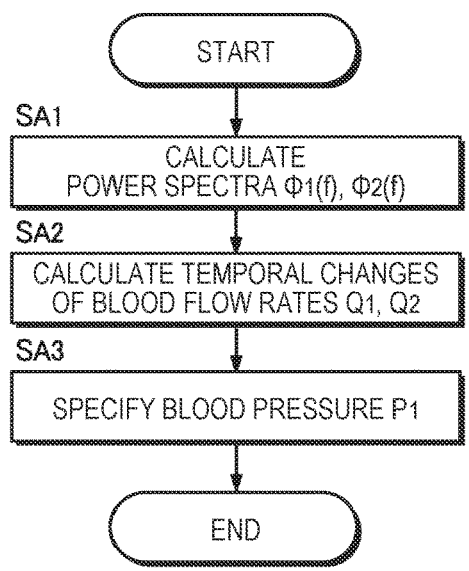
FIG. 7 is a flowchart of processing of specifying blood pressure by a specification part.

The specification part 32 specifies the blood pressure of the subject from the first detection signal S1 and the second detection signal S2 generated by the detection device 26. FIG. 7 is a flowchart of processing (hereinafter, referred to as analytical processing) of specifying the blood pressure by the specification part 32. For example, the analytical processing in FIG. 7 is repeatedly executed in a sufficiently shorter cycle for the pulse rate of the artery A.

When the analytical processing is started, the specification part 32 calculates a power spectrum $\Phi 1(f)$ with respect to the first detection signal S1 and a power spectrum $\Phi 2(f)$ with respect to the second detection signal S2 (SA1). For the calculation of the power spectra $\Phi 1(f)$, $\Phi 2(f)$, a known technique such as fast Fourier transform (FFT) may be arbitrarily employed.

Figure 6:
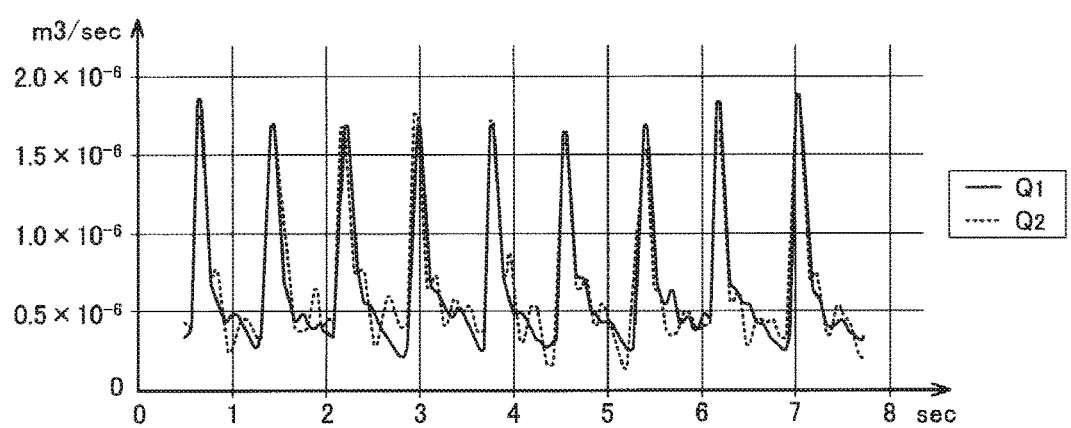
FIG. 6 is an explanatory diagram showing temporal changes of blood flow rate calculated from a first detection signal and temporal changes of blood flow rate calculated from a second detection signal.

The specification part 32 obtains a temporal change of the blood flow rate Q1 from the calculated power spectrum $\Phi 1(f)$ and obtains a temporal change of the blood flow rate Q2 from the calculated power spectrum $\Phi 2(f)$ (SA2). The blood flow rates Q1, Q2 are expressed by the following equation (1), for example. fd is a frequency of a beat signal generated by interferences between scattered light from the stationary tissues and scattered light from the moving blood cells. I is light reception intensity of the light receiving parts R. For example, when the blood flow rates Q1, Q2 are calculated with respect to each 0.1 msec, the temporal change of the blood flow rate Q1 and the temporal change of the blood flow rate Q2 exemplified in FIG. 6 are calculated.

$$Q = \frac{\int f_d \cdot \Phi(f_d) df_d}{I^2} \quad (1)$$

The specification part 32 calculates blood pressure P1 on the upstream side (i.e., the first light receiving part R1 side) from the calculated blood flow rate Q1 and blood flow rate Q2 (SA3). For example, the blood pressure P1 is expressed by the following equation (2). Zc is impedance of the artery A, ω is an angular frequency, γ is a propagation constant, λ is a distance between two points of the first light receiving part R1 and the second light receiving part R2 (i.e., a sum of the distance δ1 and the distance δ2).

$$P_1(\omega) = Z_C \frac{Q_1(\omega)\cosh\gamma\lambda - Q_2(\omega)}{\sinh\gamma\lambda} \quad (2)$$

The propagation constant $\gamma$ is expressed by the following equation (3). C is compliance of the artery A, $\psi$ is vascular resistance, L is inertance of the artery A, $\rho$ is density of blood, $\zeta$ is a vascular cross-sectional area, $\eta$ is a coefficient of viscosity, and PWV is a pulse wave velocity. The density $\rho$ varies little among individuals and is set to a predetermined value (e.g. 105 Kg/m$^3$). The vascular cross-sectional area $\zeta$ is calculated using e.g. a statistical value (2.5 mm to 3.0 mm) of the vascular diameter in the radial arteries of adults. The coefficient of viscosity $\eta$ varies little among individuals and is set to a predetermined value (e.g. 0.004 Pa·S). The pulse wave velocity PWV can be calculated by e.g. division of the distance between two points $\lambda$ by an amount of shift $\Delta T$ between the waveform rise times of the blood flow rate Q1 and blood flow rate Q2 exemplified in FIG. 6 (PWV=$\lambda/\Delta T$).

$$\gamma = \sqrt{j\omega C(\Psi + j\omega L)} = \sqrt{j\omega \frac{8\pi\eta}{\rho \cdot \zeta \cdot PWV^2} - \frac{\omega^2}{PWV^2}} \quad (3)$$

The impedance Zc of the equation (2) is expressed by the following equation (4).

$$Z_C = \sqrt{\frac{\Psi + j\omega L}{j\omega C}} = \sqrt{\left(\frac{\rho \cdot PWV}{\zeta}\right)^2 - j\frac{8\pi\eta\rho PWV^2}{\omega\zeta^3}} \quad (4)$$

The specification part 32 generates a time sequence of the blood pressure P1 (i.e. blood pressure waveform) by repeating the analytical processing exemplified as above in a predetermined cycle. The reporting part 34 allows the display device 24 to display the blood pressure P1 specified by the specification part 32. Specifically, the reporting part 34 specifies the highest blood pressure and the lowest blood pressure from the blood pressure waveform generated by the specification part 32 and allows the display device 24 to display the highest blood pressure and the lowest blood pressure. Note that a configuration in which the reporting part 34 reports a warning to the user when the blood pressure P1 changes to a numeric value beyond the predetermined range is also preferable.

As described above, in the embodiment, the light emitting part E, the first light receiving part R1, and the second light receiving part R2 are located on the straight line X along the artery A, and thereby, for example, compared to a configuration in which the light emitting part E, the first light receiving part R1, and the second light receiving part R2 are not along the artery A, the first light receiving part R1 and the second light receiving part R2 easily receive the coherent light passing through the artery A. Therefore, the detection signals S for higher-accuracy specification of the biological information on the blood flow of the artery A can be generated. Further, in the embodiment, the respective first light receiving part R1 and second light receiving part R2 are provided in the positions at which the distances $\delta$ from the light emitting part E are equal. According to the above described configuration, the coherent light passes through at the nearly equal depths D inside of the measurement site M, and thereby, compared to a configuration including two light receiving parts at distances from the light emitting part E different from each other, the detection signals S for higher-accuracy specification of the biological information on the blood flow of the artery A may be generated. As will be understood from the above explanation, in the embodiment, the biological information on the blood flow of the artery A may be specified with higher accuracy.

For example, when detection signals are generated from micro vessels such as capillaries existing in a wide range, it is necessary to provide many light receiving parts. On the other hand, according to the configuration of the embodiment in which the detection signals S of the artery A extending in a thicker and narrower range than that of the micro vessels, compared to the configuration of generating the detection signals from the micro vessels, the number of light receiving parts maybe reduced. In addition, downsizing and power saving of the detection device 26 and the measuring apparatus 100 can be realized.

Modified Examples

The embodiment exemplified as above may be variously modified. The specific modified forms will be exemplified as below. Two or more forms arbitrarily selected from the following exemplifications can be appropriately combined.

(1) In the above described embodiment, the configuration in which the belt 14 is wound around the entire circumference of the measurement site M is exemplified, however, a configuration in which the belt 14 is wound around only a part of the measurement site M may be employed.

(2) In the above described embodiment, the blood pressure is measured, however, the kind of biological information on blood flow is not limited to the above described exemplification. For example, a configuration in which the pulse wave velocity PWV is measured as the biological information on the blood flow may be employed. Note that the pulse wave velocity PWV is preferably used as an index of arteriosclerosis.

Figure 8:
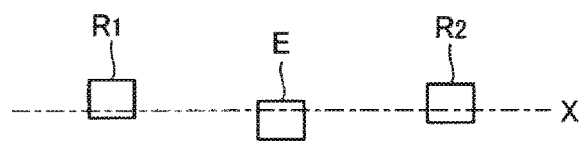
FIG. 8 is an explanatory diagram of a position relationship between the light emitting part, the first light receiving part, and the second light receiving part in a modified example.

(3) In the above described embodiment, the configuration in which the respective centers of the light emitting part E, the first light receiving part R1, and the second light receiving part R2 are located on the straight line X is exemplified, however, the positions of the light emitting part E, the first light receiving part R1, and the second light receiving part R2 on the straight line X are not limited to the above described exemplification. For example, as exemplified in FIG. 8, even a configuration in which the centers of the light emitting part E, the first light receiving part R1, and the second light receiving part R2 are not located on the straight line X, if the respective parts partially overlap with the straight line X in the plan view, the light emitting part E, the first light receiving part R1, and the second light receiving part R2 may be located on the straight line X. Note that, according to the above described embodiment in which the respective centers of the light emitting part E, the first light receiving part R1, and the second light receiving part R2 are located on the straight line X, the advantage that the detection signals S that enable higher-accuracy specification of the biological information may be generated is remarkably significant.

(4) In the above described embodiment, the configuration in which the light emitting part E, the first light receiving part R1, and the second light receiving part R2 all completely overlap with the artery A in the plan view is exemplified, however, the configuration in which the respective light emitting part E, first light receiving part R1, and second light receiving part R2 overlap with the artery A is not essential. That is, the position of the straight line X with respect to the artery A is not limited to the above described exemplification, but a configuration in which the light emitting part E, the first light receiving part R1, and the second light receiving part R2 do not overlap with the artery A in the plan view may be employed. That is, the configuration in which the light emitting part E, the first light receiving part R1, and the second light receiving part R2 do not overlap with the artery A in the plan view may be employed as long as the coherent light output from the light emitting part E may reach the first light receiving part R1 and the second light receiving part R2 with light reception intensity that can ensure predetermined accuracy in the specification of the biological information on the blood flow. Note that, according to the above described embodiment in which the light emitting part E, the first light receiving part R1, and the second light receiving part R2 overlap with the artery A, higher light reception intensity may be obtained, and thereby, there is an advantage that the biological information may be specified with higher accuracy.

(5) In the above described embodiment, the measuring apparatus 100 generates and displays the biological information, however, a separate apparatus from the measuring apparatus 100 can generate and display the biological information. For example, generation and display of the biological information can be realized using a terminal apparatus (e.g. cell phone or smartphone) communicable with the measuring apparatus 100. Specifically, the measuring apparatus 100 generates and transmits the first detection signal S1 and the second detection signal S2 to the terminal apparatus. The terminal apparatus generates the biological information on the blood flow from the first detection signal S1 and the second detection signal S2 received from the measuring apparatus 100, and allows the display device 24 of the terminal apparatus to display the information. According to the modified example, a configuration in which one or both of the memory device 22 and the display device 24 are provided in the terminal apparatus can be employed. Or, a configuration in which one or both of the specification part 32 and the reporting part 34 are provided in the terminal apparatus (e.g. a configuration realized by an application executed in the terminal apparatus) may be employed. As will be understood from the above explanation, the measuring apparatus 100 may be realized by a plurality of apparatuses separately formed from one another.

Figure 9:
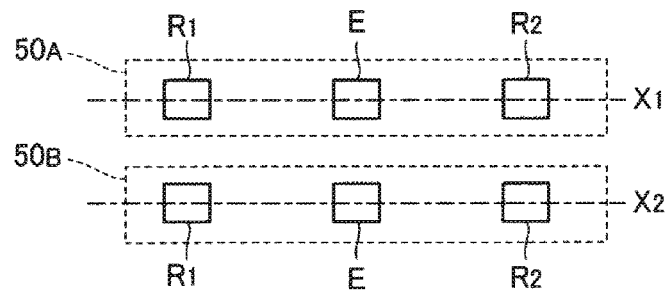
FIG. 9 is an explanatory diagram of a position relationship between the light emitting part, the first light receiving part, and the second light receiving part in a modified example.

(6) In the above described embodiment, the configuration including the light emitting part E, the first light receiving part R1, and the second light receiving part R2 located on the single straight line X along the artery A is exemplified, however, a configuration including a plurality of sets of the light emitting part E, the first light receiving part R1, and the second light receiving part R2 may be employed. For example, in a configuration exemplified in FIG. 9, a plurality of detection parts 50 corresponding to straight lines X (X1, X2) parallel to each other are provided. In FIG. 9, the detection part 50A and the detection part 50B are exemplified for convenience, however, three or more detection parts 50 can be provided. Each of the plurality of detection parts 50 has the light emitting part E, the first light receiving part R1, and the second light receiving part R2. The light emitting part E, the first light receiving part R1, and the second light receiving part R2 in any one detection part 50 are located on the straight line X corresponding to the detection part 50. Specifically, the light emitting part E, the first light receiving part R1, and the second light receiving part R2 of the detection part 50A are located on the straight line X1 and the light emitting part E, the first light receiving part R1, and the second light receiving part R2 of the detection part 50B are located on the straight line X2. The straight line X1 and the straight line X2 extend in parallel to each other at a predetermined distance. The straight line X1 is located near e.g. a radial artery and the straight line X2 is located near e.g. an ulnar artery. As described above, the straight line X1 connecting the first light receiving part R1 and the second light receiving part R2 of the detection part 50A (an exemplification of one detection part) and the straight line X2 connecting the first light receiving part R1 and the second light receiving part R2 of the detection part 50B (an exemplification of the other detection part) are parallel to each other on the detection surface 28.

In the configuration of FIG. 9, biological information can be specified from respective detection signals S (S1, S2) generated by the light emitting part E and the respective light receiving parts R on the straight line X1 and detection signals S (S1, S2) generated by the light emitting part E and the respective light receiving parts R on the straight line X2. According to the above described configuration, of the detection signals S generated by the light receiving parts R located on the respective straight lines X, the detection signals S that enable higher-accuracy specification of biological information (e.g. the detection signals S having higher SN-ratios) can be selected for specification of biological information. Or, a configuration in which average values of biological information of both are calculated as definitive biological information may be employed. As will be understood from the above explanation, according to the configuration including the plurality of detection parts 50, compared to the above described embodiment including the light emitting part E, the first light receiving part R1, and the second light receiving part R2 located on the single straight line X, the plurality of detection signals S according to the states of the different positions of the living organism can be generated. Note that different distances δ from one another may be employed for the light emitting part E and the light receiving parts R with respect to each of a plurality of straight lines X.

(7) In the above described embodiment, the measuring apparatus 100 including the belt 14 and the casing part 12 is exemplified, however, the specific form of the measuring apparatus 100 is arbitrary. For example, the measuring apparatus 100 having any form such as a patch-type that can be attached to the body of the subject, an earring-type that can be worn on the auricle of the subject, a finger-worn-type (e.g. nail-worn-type) that can be worn on the finger tip of the subject, or a head-mounted type that can be worn on the head of the subject may be employed. Note that, for example, the possibility of interferences with daily activities is assumed when the measuring apparatus 100 of the finger-worn-type or the like is worn, and therefore, in view of constant measurement without interferences with daily activities, the measuring apparatus 100 in the above described form that can be worn on the wrist of the subject with the belt 14 is particularly preferable. Or, measuring apparatuses 100 having forms mounted (externally mounted, for example) on various electronic apparatuses such as wrist watches may be realized.

(8) The preferred embodiments of the invention may be specified as the detection device 26 alone. The detection device 26 is e.g. a sensor module in which the light emitting part E, the first light receiving part R1, and the second light receiving part R2 are provided on a substrate.

The entire disclosure of Japanese Patent Application No. 2016-139673 is hereby incorporated herein by reference.

What is claimed is:

1. A detection device that generates a first detection signal and a second detection signal used for specification of biological information on blood flow of a measurement site, comprising:
   a light emitting part that outputs coherent light;
   a first light receiving part that generates the first detection signal according to a light reception level of the coherent light output from the light emitting part and passing through an artery of the measurement site; and
   a second light receiving part that generates the second detection signal according to the light reception level of the coherent light output from the light emitting part and passing through the artery,
   wherein the light emitting part, the first light receiving part, and the second light receiving part are provided on a detection surface facing the measurement site and located on a straight line, and the first light receiving part and the second light receiving part are located at an equal distance from the light emitting part on opposite sides to each other with the light emitting part in between.

2. The detection device according to claim 1, wherein the first light receiving part and the second light receiving part are located at a distance from 0.5 mm to 3 mm from the light emitting part.

3. The detection device according to claim 1, wherein the first light receiving part and the second light receiving part are located at a distance from 1 mm to 1.5 mm from the light emitting part.

4. A detection device that generates detection signals used for specification of biological information on blood flow of a measurement site comprising a plurality of detection parts, each of the plurality of detection parts includes:
   a light emitting part that outputs coherent light;
   a first light receiving part that generates a first detection signal according to a light reception level of the coherent light output from the light emitting part and passing through the measurement site; and
   a second light receiving part that generates a second detection signal according to the light reception level of the coherent light output from the light emitting part and passing through the measurement site,
   wherein the light emitting part, the first light receiving part, and the second light receiving part are provided on a detection surface facing the measurement site and located on a straight line, and the first light receiving part and the second light receiving part are located at an equal distance from the light emitting part on opposite sides to each other with the light emitting part in between, and
   of the plurality of detection parts, a straight line connecting the first light receiving part and the second light receiving part of one detection part and a straight line connecting the first light receiving part and the second light receiving part of the other detection part are parallel to each other on the detection surface.

5. A measuring apparatus that specifies biological information on blood flow of a measurement site, comprising:
   a light emitting part that outputs coherent light to the measurement site;
   a first light receiving part that generates a first detection signal according to a light reception level of the coherent light output from the light emitting part and passing through an artery of the measurement site;
   a second light receiving part that generates a second detection signal according to the light reception level of the coherent light output from the light emitting part and passing through the artery; and
   a specification part that specifies the biological information from the first detection signal and the second detection signal,
   wherein the light emitting part, the first light receiving part, and the second light receiving part are provided on a detection surface facing the measurement site and located on a straight line, and the first light receiving part and the second light receiving part are located at an equal distance from the light emitting part on opposite sides to each other with the light emitting part in between.

6. A measuring apparatus that specifies biological information on blood flow of a measurement site, comprising:
   a belt for attaching the measuring apparatus to the measurement site;
   a light emitting part that outputs coherent light to the measurement site;
   a first light receiving part that generates a first detection signal according to a light reception level of the coherent light output from the light emitting part and passing through an artery of the measurement site;
   a second light receiving part that generates a second detection signal according to the light reception level of the coherent light output from the light emitting part and passing through the artery; and
   a specification part that specifies the biological information from the first detection signal and the second detection signal,
   wherein the light emitting part, the first light receiving part, and the second light receiving part are provided on a detection surface facing the measurement site and located on a straight line along a width direction of the belt, and the first light receiving part and the second light receiving part are located at an equal distance from the light emitting part on opposite sides to each other with the light emitting part in between.

* * * * *